United States Patent
Luchterhandt et al.

(10) Patent No.: US 6,767,935 B1
(45) Date of Patent: Jul. 27, 2004

(54) ADHESIVE SYSTEMS

(75) Inventors: Thomas Luchterhandt, Greifenberg (DE); Rainer Guggenberger, Herrsching (DE); Hendrik M. Grupp, Gilching (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/048,943

(22) PCT Filed: Jul. 28, 2000

(86) PCT No.: PCT/EP00/07272

§ 371 (c)(1),
(2), (4) Date: Jun. 17, 2002

(87) PCT Pub. No.: WO01/10388

PCT Pub. Date: Feb. 15, 2001

(30) Foreign Application Priority Data

Aug. 6, 1999 (DE) .......................... 199 37 091

(51) Int. Cl.⁷ .............................. C08F 2/46; A61K 6/08
(52) U.S. Cl. ................ 522/100; 522/168; 522/170; 522/182; 522/113; 522/122; 522/121; 522/908; 523/113; 523/115; 523/116; 523/109; 523/300
(58) Field of Search ................ 522/100, 168, 522/170, 182, 113, 122, 121, 908; 523/113, 116, 115, 300, 109

(56) References Cited

U.S. PATENT DOCUMENTS 5,151,479 A * 9/1992 Mukai et al. ............... 526/277
6,126,922 A * 10/2000 Rozzi et al. ................. 424/49

FOREIGN PATENT DOCUMENTS

| DE | 4439485 | 4/1998 |
|----|---------|--------|
| DE | 19648283 | 5/1998 |
| DE | 19714324 | 10/1998 |
| EP | 0678533 | 10/1995 |
| EP | 0712622 | 5/1996 |
| EP | 0897710 | 2/1999 |
| WO | 98/45197 | 10/1998 |
| WO | 98/47046 | 10/1998 |
| WO | 98/47047 | 10/1998 |
| WO | 99/03444 | 1/1999 |
| WO | 00/5680 | 9/2000 |

* cited by examiner

*Primary Examiner*—James J. Seidleck
*Assistant Examiner*—Sanza L. McClendon
(74) *Attorney, Agent, or Firm*—Crowell & Moring LLP

(57) ABSTRACT

The invention relates to the utilization of an adhesive system containing at least one component i) which is capable of initiating cationic polymerization and is selected from unsaturated carbonic acids and their anhydrides or acid chlorides, unsaturated phosphoric acids and their esters, unsaturated phosphonic acids and their esters, unsaturated sulfonic acids and their esters, and strong inorganic acids, and at least one component, ii) that can undergo cationic polymerisation for the hardening of radical or cationic or radical and cationically curable materials on laminated fabric which contains water.

15 Claims, No Drawings

ADHESIVE SYSTEMS

The present invention relates to adhesive systems based on cationically curing compounds, and to their use.

In polymerizable dental compositions, use has to date been made predominantly of methacrylate monomers and acrylate monomers. Particular attentiveness is deserved by 2,2-bis[4-(2-hydroxy-3-methacryloyloxypropoxy)-phenyl] propane (bis-GMA), described by Bowen [U.S. Pat. No. 3,066,112]. Mixtures of this methacrylate with triethylene glycol dimethacrylate are still used even today as a standard formulation for dental plastic direct filling materials. Methacrylic derivatives of the diformylated bis(hydroxymethyl) tricyclo-[5.2.1.0$^{2,6}$]decane are also established as monomers for dental composites [W. Gruber et al., DE-A-27 14 538; W. Schmitt et al., DE-A-28 16 823; J. Reiners et al., EP-A-0 261 520]. A significant disadvantage of these dental compositions, however, is the high volume shrinkage that occurs as a result of the polymerization. This shrinkage may be minimized, for example, through the use of ring-opening monomers, such as the cationically curing epoxides.

Concerning cationically curable epoxide compositions for dental applications, little is known: U.S. Pat. No. 5,556, 896 describes epoxide-containing compositions which are necessarily required to include spiroorthocarbonates as shrinkage-compensating monomers. Bowen describes a composition comprising quartz sand and an aliphatic diepoxide (bisphenol A diglycidyl ether) which in the cured state is said to have good stability in the oral environment [J. Dent. Res. 35, 1956, 360–379]. AT-A-204 687 describes epoxide dental compositions based on bisphenol A which are cured by means of Lewis acid catalysts. The documents DE-A-196 48 283, WO-96/13538 and WO-95/30402 likewise describe polymerizable dental compositions based on epoxides, and their use.

Although extensive experience exists with epoxides and cycloaliphatic epoxides (U.S. Pat. No. 2,716,123, U.S. Pat. No. 2,750,395, U.S. Pat. No. 2,863,881, U.S. Pat. No. 3,187,018), such monomers, and cationically polymerizable compositions formulated from them, have at no point in time been available commercially with the properties required for dental applications.

The reason for this is the fact that the curing of these cationically polymerizing compositions is inhibited by water and the hard tooth substance, such as in dentine, contains from about 11 to 16 percent by weight of water (G.-H. Schumacher et. al., Anatomie und Biochemie der Zähne, Gustav Fischer Verlag, 1990, 4$^{th}$ edition). Accordingly, it is easy to explain that, for example, formulations of dental filling materials on an epoxide basis are unable to exhibit inherent adhesion to dentine, and so the use of such materials was impossible.

In order to affix (meth)acrylate-based dental filling materials—i.e., free-radically curing systems—use is made of what are known as adhesive systems.

The quality of these adhesive systems is reflected in the following criteria:
  complete adhesion to the hard tooth substance, without defects ("sealing");
  complete adhesion to the filling material,
  permanent bond.

In view of the circumstances set out above, the curing of cationically crosslinking systems on the hard tooth substance is unlikely. An adhesive system on a cationically crosslinking basis for compositions (including those) that cure cationically has never been available commercially on the market.

DE-A-197 43 564, it is true, describes radiation-curable adhesion promoter—so-called primer—compositions based on solvent-free, cationically and/or free-radically curable crosslinking systems; however, these systems are used only to coat water-free materials, examples being plastics, such as polyvinylidene chloride (PVDC) or silicone.

WO-98/47046 describes epoxy-based photopolymerizable mixtures comprising an epoxy resin, an iodonium salt, a transfer molecule sensitive in visible light, and an electron donor and claims their use as a dental adhesive system. However, it is found that with such mixtures it is impossible to obtain adhesion to cationically curing mixtures on the hard tooth substance (see comparative mixtures 1 to 3 of the present specification).

WO-99/34766 states that compositions with a high proportion of cationically curable groups adhere very poorly if at all to hard tooth tissue. To solve the problem, it is proposed to provide either a hybrid composition comprising constituents containing free-radically and cationically polymerizable groups or a composition which is substantially free from cationically polymerizable groups.

It is a primary object of the present invention to provide an alternative adhesive system which solves the abovementioned problems and can be adhered preferably to water-containing hard tissue, such as tooth.

In accordance with the invention, this object is achieved through the use of adhesive systems comprising at least one component i) capable of initiating a cationic polymerization and selected from inorganic acids having a pKA of less than 4.90, preferably less than 4.80, unsaturated carboxylic acids and their anhydrides or acid chlorides, unsaturated organic phosphoric acids and their esters, unsaturated organic phosphonic acids and their esters, unsaturated organic sulfonic acids and their esters, and at least one component ii) which is cationically polymerizable.

It has surprisingly been found that, when using cationically polymerizable adhesive systems with photopolymerization initiators such as are described in WO-98/47046 to affix cationically curing materials to water-containing hard tissue, adequate adhesion is oil unobtainable (see comparison mixtures 1 to 3 of the present specification).

This can be done only using adhesive systems which comprise the specific acids mentioned above and described hereinbelow.

Additionally, the photopolymerization inhibitors described in the aforementioned WO-98/47046, composed of an iodonium salt, a transfer molecule which is sensitive in visible light, and an electron donor, and also, for example, the cationic polymerization initiators described in DE-A-197 36 471 and DE-A-197 43 564, may be present.

It has further been found that a particularly advantageous method of affixing aforementioned materials to aforementioned hard tissue comprises using free-radically crosslinkable materials as acids and additionally conducting a free-radical crosslinking. In this way, the cationically crosslinkable groups are very largely retained for copolymerization with the filling material in the boundary layer.

A further adhesion-promoting effect of this reaction regime is the development of the "lubricating layer" which is known to form in free-radically crosslinking systems. This layer comes about as a result of oxygen inhibition and provides for optimum mixing at the boundary between adhesive and filling system.

The invention is described in more detail below.

The terms "comprise" and "embrace" as used in the invention introduce a nonexhaustive listing of features.

The adhesive mixtures which have the advantages described when used in accordance with the invention comprise as constituent i) preferably from 0.01 to 95% by weight, in particular from 0.1 to 90% by weight; and with particular preference from 0.1 to 80% by weight of an initiator system which is selected from the specific acids described above, and as constituent ii) preferably from 5 to 99.99% by weight, in particular from 10 to 99.90% by weight, and with particular preference from 20 to 99.90% by weight, of a cationically polymerizable material.

In one preferred embodiment, the acids are themselves free-radically polymerizable and the overall mixture further comprises an initiator capable of initiating the free-radical polymerization.

Initiators suitable as component i) include the following cationic initiators:

Unsaturated carboxylic acids, such as mono- or polyunsaturated organic monocarboxylic, dicarboxylic or polycarboxylic acids, or precursors thereof which can form acids with water, such as anhydrides or acid chlorides, including in particular acidic methacrylic esters or amides.

Preference is given to unsaturated carboxylic acids of the following formula:

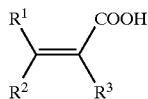

in which: $R^1$, $R^2$, $R^3$=H, $C_1$ to $C_{25}$ alkyl or cycloalkyl radicals, unsubstituted or substituted by N, O, S, Si, P or halogen, or aromatic $C_6$ to $C_{12}$ radicals or heterocyclic $C_3$ to $C_{12}$ radicals with N, O, S, P and unsubstituted or substituted by halogen.

It is also possible to use acids, such as 4-methacryloyloxyethyltrimellitic acid or its anhydrides (Takeyama, M. et al., J.Jap.Soc. f. Dent. App. A. Mat. 19, 179 (1978)), or the reaction products of trimellitic chloride anhydride with amine-type, thiol-type or hydroxyl-type (meth)acrylic esters, such as 2-hydroxyethylene methacrylate or methacroyloxyethyl o-phthalate.

Unsaturated organic phosphoric and phosphonic acids.

Preference is given, for example, to unsaturated organic esters of monofluorophosphonic acids, such as are described in U.S. Pat. No. 3,997,504, unsaturated organic esters of phosphorus acids containing chlorine or bromine attached directly to the phosphorus, such as are described in EP-A-0 058.483, unsaturated organic esters of phosphoric acid which are present in the form of cyclic pyrophosphates (anhydrides), such as are described in DE-A-3 048 410, and unsaturated organic esters of phosphoric or phosphonic acids, such as are described in DE-A-2 711234 and DE-A-3 150 285. Equally preferred are the hydrolysis-stable, polymerizable acryloylphosphonic acids of DE-A-19 746 708.

Also suitable are the monomers containing phosphoric acid groups such as described in U.S. Pat. No. 4,182,035, U.S. Pat. No. 4,222,780, U.S. Pat. No. 4,235,633, U.S. Pat. No. 4,359,117 and U.S. Pat. No. 4,368,043 and also in EP-A-0 084 407. In the adhesive mixtures of the invention, it is preferred to use ethylenically unsaturated phosphoric esters in accordance with the following formula:

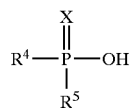

in which:
X=O, S;
$R^4$ and $R^5$ independently of one another are H, OH, or $C_1$ to $C_{25}$ alkyl or cycloalkyl, unsubstituted or substituted or bridged by heteroatoms such as N, halogen, Si, O or S, aromatic $C_6$ to $C_{12}$ radicals and/or heterocyclic $C_4$ to $C_{12}$ radicals, or substituted by acrylic esters, it also being possible for the radicals $R^4$ and $R^5$ independently of one another to be attached to the phosphorus via O, or

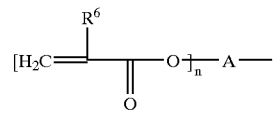

where
$R^6$ is hydrogen or $C_1$ to $C_6$ alkyl,
n is an integer $\geq 1$, and
A is a divalent $C_1$ to $C_{25}$ alkylene or cycloalkylene radical, substituted or unsubstituted or bridged by N, O, S, Si, P or halogen or an aromatic $C_6$ to $C_{12}$ radical and/or heterocyclic $C_4$ to $C_{12}$ radical containing N, O, S, or P and unsubstituted or substituted by halogen, with the proviso that the radical that contains $R^6$ is present at least once.

Substituted, unsaturated organic sulfonic acids and their esters.

Inorganic acids having a pKA of less than 4.90, preferably less than 4.80, such as mineral acids, especially phosphoric acid and hydrofluoric acid, superacids, such as $HSbF_6$ or $HBF_4$, Lewis acids, such as $BF_3$ adducts, metal salts, such as $FeCl_3$, $ZnCl_2$, or complex acids or precursors of acids, such as acid chlorides or anhydrides.

The aforementioned cationic initiator systems may be used alone or else in mixtures, and in this context the listings should be understood as being by way of example and in no way exhaustive.

As component ii) in the adhesive mixtures of the invention it is possible to use cationically curing materials which are selected from the following groups. In this context, this listing as well is to be understood as being by way of example and not exhaustive.

Epoxy resins, such as those described in DE-A-196 48 283 Al, especially 1,3,5,7-tetra-kis(2,1-ethanediyl-3,4-epoxycyclohexyl)-1,3,5,7-tetramethylcyclotetrasiloxane.

Spiro-ortho-carbonates, such as 3,9-diethyl-3,9-dipropionyloxymethyl-1,5,7,11-tetraoxaspiro-[5.5] undecane, 2,8-dimethyl-1,5,7,11-tetraoxa-spiro[5.5] undecane, or 5,5-diethyl-19-oxadispiro[1,3-dioxane-2-2'-1,3-doixane-5',4''-bi-cyclo[4.1.0]heptane, such as are described in U.S. Pat. No. 5,556,896, or spiro-ortho-esters, or oxetanes, such as are described in DE-A-197 36 471 p. 3 f., or vinyl ethers, such as alkyl or cycloalkyl vinyl ethers, ethylene glycol divinyl ether, triethylene glycol divinyl ether, glycidyl vinyl ether or butanediol vinyl ether.

The aforementioned materials may be used alone or else in mixtures.

Furthermore, if desired, free-radically curing compounds which contain no acid groups may be admixed, preferably in an amount of less than 25% by weight. This embodiment leads to the formation of an interpenetrating network.

An amount of free-radically polymerizable compounds that is less than the amount of cationically polymerizable compounds ensures that the matrix properties of the network of cationically polymerized compounds predominantly determine the properties of the adhesive system.

Typical monomers or prepolymers which cure by the free-radical chain mechanism and may be present in component ii) are acrylates or methacrylates. Suitable, for example, are monofunctional and polyfunctional (meth)-acrylate monomers. Typical representatives of this class of compound (DE-A-4 328 960) are alkyl (meth)acrylates, including the cycloalkyl (meth)-acrylates, aralkyl (meth)acrylates and 2-hydroxyalkyl (meth)acrylates, examples being hydroxypropyl methacrylate, hydroxyethyl methacrylate, isobornyl acrylate, isobornyl methacrylate, butyl glycol methacrylate, acetyl glycol methacrylate, triethylene glycol dimethacrylate, polyethylene glycol dimethacrylate, 2-phenylethyl methacrylate, 2-ethylhexyl methacrylate, cyclohexyl methacrylate, lauryl, methacrylate and hexanediol di(meth)acrylate. Use may also be made of the long-chain monomers, such as are described in U.S. Pat. No. 3,066,112, based on bisphenol A and glycidyl methacrylate or derivatives thereof formed by addition reaction with isocyanates. Also suitable are compounds of the bisphenyl A diethyloxy(meth)acrylate and bisphenol A dipropyloxy(meth)acrylate types. It is also possible for the oligoethoxylated and oligopropoxylated bisphenol A diacrylic and dimethacrylic esters to find application. Also highly suitable are the compounds mentioned in DE-A-2 816 823 that are diacrylic and dimethacrylic esters of bis(hydroxymethyl)tri-cyclo[$5.2.1.0^{2,6}$]decane and the diacrylic and dimethacrylic esters of compounds of bis (hydroxymethyl)tricyclo[$5.2.1.0^{2,6}$]decane extended by from 1 to 3 ethylene oxide and/or propylene oxide units. It is also possible to use mixtures of said monomers.

Where ethylenically unsaturated groups are additionally present in component i) or free-radically polymerizable compounds are admixed, then it is also possible to use initiators which are mandatorily additionally free-radical initiators.

The radical-forming initiators which may be present in the mixtures are described in the literature (e.g. J.-P. Fouassier, Photoinitiation, Photopolymerization and Photocuring, Hanser Publishers, Munich, Vienna, New York 1995 or else J.-P. Fouassier, J. F. Rabek (eds.), Radiation Curing in Polymer Science and Technology, Vol. II, Elsevier Applied Science, London, New York, 1993). They may be substances which can be activated by UV light or visible light, such as benzoin alkyl ethers, benzil ketals, acylphosphine oxides or aliphatic and aromatic 1,2-diketone compounds, an example being camphorquinone, it being possible to accelerate the catalyst activity conventionally by adding activators, such as tertiary amines or organic phosphites.

Examples of suitable initiator systems for triggering the free-radical polymerization by way of a redox mechanism are the systems comprising peroxide/amine, peroxide/barbituric acid derivatives or peroxide/acids and the like. When using such initiator systems it is appropriate to keep ready an initiator (e.g., peroxide) and a catalyst component (e.g., amine) separately. The two components are then mixed homogeneously with one another shortly before their use.

The adhesive systems of the invention may also comprise fillers, dyes, flow modifiers, stabilizers, solvents, ion donor substances, bactericidal or antibiotic substances, compounds which increase the X-ray opacity, or further modifiers.

Preferred diluents are solvents, such as dialkyl ketones (e.g., acetone, methyl ethyl ketone), acetyl acetone or alcohols (e.g., ethanol, propanol) or else highly mobile polymerizable substances such as 2-hydroxyethyl methacrylate or 2,3-epoxypropyl methacrylate.

Examples of suitable fillers are substances such as are used in common dental materials, with particular preference being given to quartz, Aerosils, highly disperse silicas, organic fillers or glass, or mixtures of these substances, or else those such as are described in DE-A-196 48 283 A1 (page 10, line 48 to 59).

Among the ion donor substances, preference is given to those which permit release of fluoride ions, such as fluoride salts of the first or second main group, such as sodium fluoride or calcium fluoride, or complex w fluoride salts, such as $KZnF_3$, or such as are described in EP-A-0 717 977, fluoride-donating glasses, and also mixtures of these fluoride ion sources.

Additionally, it is further possible for one or more non-polymerizable acids to be present, such as a carboxylic acid, phosphoric acid, phosphonic acid, sulfuric acid, sulfinic acid, sulfenic acid, mineral acid, Lewis acid or complex acid.

As bactericidal or antibiotic substances it is possible, for example, to use chlorhexidine, pyridinium salts or the customary pharmaceutical substances, such as β-lactam antibiotics (penicillins), cephalosporins, tetracyclines, ansamycins, canamycins, chloramphenicol, fosfomycin, antibacterial macrolides, polypeptide antibiotics, chemotherapeutics, such as sulfonamides, dihydrofolate reductase inhibitors, nitrofuran derivatives or gyrase inhibitors.

Where the adhesive mixtures comprise additives above and beyond components i) and ii), these additives may be present, individually or mixed, in amounts of from 0.1% by weight to 90% by weight, the mixture being prepared such that together with components i) and ii) the ingredients add up to total 100% by weight.

Naturally, the adhesive mixtures of the invention may also be used for affixing materials which cure purely by a free-radical mechanism.

In the text below, the invention is described in more detail with reference to examples, which are to be understood as implementation examples and in no way as limiting.

The adhesion measurements were carried out on bovine dentine and are substantially higher still on bovine enamel. Adhesion Measurement on Cattle Teeth by Adhesive Affixing of a Filling Material:

The adhesive bond was tested by means of a tensile adhesion test on cattle teeth. For each test, 5 freshly extracted cattle teeth were abraded using abrasive paper to an extent such as to give a sufficiently large exposed area of dentine. To each of these areas, wax platelets with a punched-out hole of 6 mm were stuck in order to obtain a standardized adhesion area. In accordance with customary practice, the test area was then etched for 20 seconds using a customary phosphoric acid solution (Minitipg etching gel, ESPE Dental AG, Seefeld) for 20 seconds and then rinsed off with water. An amount of the test mixtures sufficient to fully wet the test surface was incorporated onto the areas of dentine thus pretreated, using a microbrush, for 20 seconds, followed by brief blowing with compressed air, and were polymerized by means of a light polymerization device (Elipar Highlight®, ESPE) for 20 seconds. The cationically curing filling material (either the cationic filling material whose preparation is described below or commercially customary Pertac II (ESPE Dental AG, Seefeld)) was then introduced into the cutouts in the wax platelets and polymerized by exposure for 40 seconds. The wax platelets were removed and the test bodies were stored for 24 h at 36° C. and 100% atmospheric humidity. The test bodies were then pulled off in a tensile test (Zwick universal testing machine).

The adhesion values determined in this test are given in Table 1.

Preparation of a Cationically Curing Filling Material:

In a three-finger kneading apparatus, the following ingredients are kneaded to a homogeneous paste. The following are used for 100 g of paste:

- 75.000% by weight (75.000 g) quartz (average particle size 0.9 μm, silanized with 5% by weight glycidyloxypropyltrimethoxysilane);
- 0.525% by weight (0.525 g) 4-methylphenyl-4-isopropylphenyliodonium tetrakis(pentafluorophenyl)-borate;
- 0.223% by weight (0.223 g) camphorquinone (Merck, Darmstadt);
- 0.001% by weight (0.001 g) ethyl 4-dimethyl-aminobenzoate (Merck, Darmstadt);
- 0.001% by weight (0.001 g) 2-butoxyethyl 4-dimethyl-aminobenzoate;
- 12.125% by weight (12.125 g) 3,4-epoxycyclohexyl 3,4-epoxycyclohexanecarboxylate;
- 12.125% by weight (12.125 g) 1,3,5,7-tetrakis(2,1-ethanediyl-3,4-epoxycyclohexyl)-1,3,5,7-tetramethyl-cyclotetrasiloxane.

Preparation of the Inventive Adhesive Mixture 1:

To prepare 10 g of adhesive mixture 1, the following ingredients are mixed thoroughly with one another:

- 48.650% by weight (4.865 g) 1,3,5,7-tetrakis(2,1-ethanediyl-3,4-epoxycyclohexyl)-1,3,5,7-tetramethyl-cyclotetrasiloxane;
- 38.920% by weight (3.892 g) 10-methacryloyloxyethyl phosphate;
- 9.380% by weight (0.938 g) 2-hydroxyethyl methacrylate;
- 2.000% by weight (0.200 g) Rhodorsil PI 2074 (Rhone Poulenc, iodonium salt);
- 0.600% by weight (0.060 g) camphorquinone (Merck, Darmstadt);
- 0.450% by weight (0.045 g) ethyl-4-dimethylamino-benzoate (Merck, Darmstadt);

Preparation of the Inventive Adhesive Mixture 2:

To prepare 10 g of adhesive mixture 1, the following ingredients are mixed thoroughly with one another:

- 48.650% by weight (4.865 g) 3,4-epoxycyclohexyl 3,4-epoxycyclohexanecarboxylate;
- 38.920% by weight (3.892 g) 10-methacryloyloxyethyl phosphate;
- 9.380% by weight (0.938 g) 2-hydroxyethyl methacrylate;
- 2.000% by weight (0.200 g) Rhodorsil PI 2074 (Rhone Poulenc, iodonium salt);
- 0.600% by weight (0.060 g) camphorquinone (Merck, Darmstadt);
- 0.450% by weight (0.045 g) ethyl-4-dimethylamino-benzoate (Merck, Darmstadt);

Inventive Adhesive Mixture 3:

In this test, etching was not carried out with a customary phosphoric acid solution (Minitip® etching gel, ESPE Dental AG, Seefeld) for 20 seconds; instead, an amount of 1,3,5,7-tetrakis(2,1-ethanediyl-3,4-epoxycyclohexyl)-1,3,5,7-tetramethylcyclotetrasiloxane sufficient to wet the surface was worked in for 20 seconds using a microbrush, followed by brief blowing with compressed air, and then a 5 percent strength by weight of solution of $HSbF_6$ in ethanol was applied and blown with compressed air. The cationically curing filling material was then introduced into the cutouts in the wax platelets and polymerized by exposure for 40 seconds. The wax platelets were removed and the test bodies were stored for 24 h at 36° C. and 100% atmospheric humidity. The test bodies were then pulled off in a tensile test (Zwick universal testing machine).

Preparation of the Comparative Mixture 1:

To prepare 10 g of comparative mixture 1, the following ingredients are mixed thoroughly with one another:

- 97.300% by weight (9.730 g) 1,3,5,7-tetrakis(2,1-ethanediyl-3,4-epoxycyclohexyl)-1,3,5,7-tetramethyl-cyclotetrasiloxane;
- 2.000% by weight (0.200 g) Rhodorsil PI 2074 (Rhone Poulenc, iodonium salt);
- 0.500% by weight (0.050 g) camphorquinone (Merck, Darmstadt);
- 0.200% by weight (0.020 g) BEDB (Lambson);

Preparation of the Comparative Mixture 2:

To prepare 10 g of comparative mixture 2, the following ingredients are mixed thoroughly with one another:

- 97.300% by weight (9.730 g) 3,4-epoxycyclohexylmethyl 3,4-epoxycyclohexane carboxylate;
- 2.000% by weight (0.200 g) Rhodorsil PI 2074 (Rhone Poulenc, iodonium salt);
- 0.500% by weight (0.050 g) camphorquinone (Merck, Darmstadt);
- 0.200% by weight (0.020 g) BEDB (Lambson);

Preparation of the Comparative Mixture 3:

To prepare 10 g of comparative mixture 3, the following ingredients are mixed thoroughly with one another:

- 48.650% by weight (4.865 g) 3,4-epoxycyclohexylmethyl 3,4-epoxycyclohexane carboxylate;
- 48.650% by weight (4.865 g) 1,3,5,7-tetrakis(2,1-ethanediyl-3,4-epoxycyclohexyl)-1,3,5,7-tetramethyl-5 cyclotetrasiloxane;
- 2.000% by weight (0.200 g) Rhodorsil PI 2074 (Rhone Poulenc, iodonium salt);
- 0.500% by weight (0.050 g) camphorquinone (Merck, Darmstadt);
- 0.200% by weight (0.020 g) BEDB (Lambson);

TABLE 1

Adhesion of the adhesive mixtures described in the examples:

| Adhesive mixture | Filling material | Dentine adhesion [MPa]* |
|---|---|---|
| Adhesive mixture 1 | Cationically curing | 3.5 |
| Adhesive mixture 2 | Cationically curing | 3.7 |
| Adhesive mixture 3 | Cationically curing | 2.4 |
| Comparative mixture 1 | Cationically curing | 0.0 |
| Comparative mixture 1 | Pertac II (ESPE Dental AG, Seefeld) | 0.0 |

TABLE 1-continued

Adhesion of the adhesive mixtures described in the examples:

| Adhesive mixture | Filling material | Dentine adhesion [MPa]* |
|---|---|---|
| Comparative mixture 2 | Cationically curing | 0.0 |
| Comparative mixture 2 | Pertac II (ESPE Dental AG, Seefeld) | 0.0 |
| Comparative mixture 3 | Cationically curing | 0.0 |
| Comparative mixture 3 | Pertac II (ESPE Dental AG, Seefeld) | 0.0 |

*Average of 5 measurements each

What is claimed is:

1. A method for adhering a cationically or free-radically curing material to water-containing hard tissue, the method comprising applying to the hard-tissue an adhesive system which comprises:

a first component which is capable of initiating a cationic polymerization and is selected from the group consisting of unsaturated carboxylic acids and their anhydrides or acid chlorides, unsaturated organic phosphoric acids and their esters, unsaturated organic phosphonic acids and their esters, unsaturated organic sulfonic acids and their esters, and inorganic acids having a pKa of less than 4.90; and a second component which is cationically polymerizable, and affixing to the hard tissue the cationically or free-radically curing material.

2. A method of claim 1, wherein the first component is present in fractions of from 0.01 to 95% by weight and the second component is present in fractions of from 5 to 99.99% by weight.

3. A method of claim 1, wherein the cationically or free-radically curing material is a dental filling material, and the hard tissue is tooth.

4. A method of claim 1, wherein the adhesive system further comprises at least one additional component selected from the group consisting of (1) a further free-radical or cationic polymerization initiator or mixtures thereof; (2) a diluent; (3) a filler; (4) a fluoride ion source; (5) an acid containing no double bond; and (7) an agent having a bactericidal or antibiotic activity, and mixtures thereof.

5. A method of claim 1, wherein the first component is selected from the group consisting of (a) unsaturated carboxlyic acids of the formula:

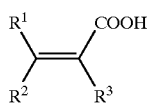

in which $R^1$, $R^2$ and $R^3$ are independently H; $C_1$ to $C_{25}$ alkyl or cycloalkyl radicals, unsubstituted or substituted by N, O, S, Si, P or halogen; aromatic $C_6$ to $C_{12}$ radicals; or heterocyclic $C_3$ to $C_{12}$ radicals with N, O, S, P and unsubstituted or substituted by halogen; and (b) ethylenically unsaturated phosphoric esters or phosphonic esters of the formula:

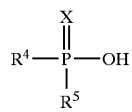

in which
X is O or S;
$R^4$ and $R^5$ independently of one another are H; or OH; or $C_1$ to $C_{25}$ alkyl or cycloalkyl, unsubstituted or substituted or bridged by heteroatoms such as N, halogen, Si, O or S; aromatic $C_6$ to $C_{12}$ radicals; or heterocyclic $C_4$ to $C_{12}$ radicals, or substituted by acrylic esters, it also being possible for the radicals $R^4$ and $R^5$ independently of one another to be attached to the phosphorous via O; or a radical of the formula

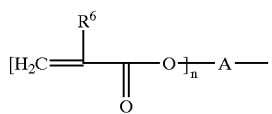

wherein $R^6$ is hydrogen or $C_1$ to $C_6$ alkyl and n is an integer $\leq 1$, and A is a divalent $C_1$ to $C_{25}$ alkyl or cycloalkyl radical, substituted or unsubstituted or bridged by N, O, S, Si, P or halogen or an aromatic $C_6$ to $C_{12}$ radical or heterocyclic $C_3$ to $C_{12}$ radical containing N, O, S or P and unsubstituted or substituted by halogen, with the proviso that the radical that contains $R^6$ is present at least once.

6. A method of claim 1, wherein the adhesive system is polymerized by supplying electromagnetic radiation.

7. A method of claim 6, wherein the electromagnetic radiation has a wavelength of from 350 to 1,000 nm.

8. A method of claim 1, wherein the adhesive system is applied to the hard tissue, which is then directly over-coated with a polymerizable material.

9. A method of claim 8, wherein the polymerizable material is polymerized exclusively cationically.

10. A method of claim 8, wherein the polymerizable material is capable of being polymerized cationically.

11. A method of claim 1, wherein the hard tissue is not itched prior to the application of the adhesive system.

12. A method for adhering a cationically or free-radically curing material to water-containing hard tissue, the method comprising affixing the cationically or free-radically curing material to the hard-tissue via an adhesive system which comprises a first component which is capable of initiating a cationic polymerization and is an inorganic acid having a pKa of less than about 4.8 and a second component which is cationically polymerizable.

13. An adhesive system comprising
a first component which is capable of initiating a cationic polymerization and is selected from the group of acidic polymerizable initiator consisting of unsaturated carboxylic acids or their anhydrides or acid chlorides, unsaturated organic phosphoric acids or their esters, unsaturated organic phosphonic acids or their esters, unsaturated organic sulfonic acids or their esters, and inorganic acids having a pKa of less than 4.90; and a second component which is cationically polymerizable.

14. A kit comprising the adhesive component of claim 13.

15. An adhesive system according to claim 13, wherein the first component is an inorganic acid having a pKa of less than 4.80.

* * * * *

UNITED STATES PATENT AND TRADEMARK OFFICE
CERTIFICATE OF CORRECTION

PATENT NO. : 6,767,935 B1
DATED : July 27, 2004
INVENTOR(S) : Luchterhandt, Thomas It is certified that error appears in the above-identified patent and that said Letters Patent is hereby corrected as shown below:

Title page,
Item [56], References Cited, FOREIGN PATENT DOCUMENTS, delete "98/45197" and insert -- 98/46197 --, therefor.

Column 1,
Line 46, delete "G.-H." and insert -- G. H. --, therefor.

Column 2,
Line 41, delete "oil" before "unobtainable".

Column 3,
Line 54, delete "EP-A-0 058.483" and insert -- EP-A-0 058 483 --, therefor.

Column 5,
Line 25, after "lauryl" delete ",".

Column 6,
Line 19, delete "w" before "fluoride".
Line 61, delete "Minitipg" and insert -- Minitip® --, therefor.

Column 8,
Line 48, delete "tetramethyl-5 cyclotetrasiloxane" and insert -- tetramethyl-cyclotetrasiloxane --, therefor.

UNITED STATES PATENT AND TRADEMARK OFFICE
CERTIFICATE OF CORRECTION

PATENT NO. : 6,767,935 B1
DATED : July 27, 2004
INVENTOR(S) : Luchterhandt, Thomas It is certified that error appears in the above-identified patent and that said Letters Patent is hereby corrected as shown below:

Column 9,
Line 47, delete "(7)" and insert -- (6) --, therefor.
Line 51, delete "carboxlyic" and insert -- carboxylic -- , therefor.

Column 10,
Line 24, delete "≤1" and insert -- ≥1 -- therefor.
Line 50, after "4.8" insert -- , --.

Signed and Sealed this

First Day of November, 2005

JON W. DUDAS
*Director of the United States Patent and Trademark Office*